(12) United States Patent
Dacosta et al.

(10) Patent No.: US 9,962,209 B2
(45) Date of Patent: May 8, 2018

(54) DEVICES AND METHOD OF ACHIEVING BONE FUSION

(71) Applicant: PARAGON 28, INC., Englewood, CO (US)

(72) Inventors: Albert Dacosta, Lone Tree, CO (US); Thomas San Giovanni, Miami, FL (US); Michael Houghton, Fort Collins, CO (US)

(73) Assignee: PARAGON 28, INC., Englewood, CO (US)

( * ) Notice: Subject to any disclaimer, the term of this patent is extended or adjusted under 35 U.S.C. 154(b) by 0 days. days.

(21) Appl. No.: 15/200,559

(22) Filed: Jul. 1, 2016

(65) Prior Publication Data

US 2016/0310189 A1    Oct. 27, 2016

Related U.S. Application Data

(62) Division of application No. 13/964,535, filed on Aug. 12, 2013, now Pat. No. 9,848,929.

(51) Int. Cl.
*A61B 17/04* (2006.01)
*A61B 17/86* (2006.01)
*A61F 2/08* (2006.01)
*A61B 17/88* (2006.01)
*A61B 17/84* (2006.01)
*A61B 17/16* (2006.01)
(Continued)

(52) U.S. Cl.
CPC ........ *A61B 17/864* (2013.01); *A61B 17/1615* (2013.01); *A61B 17/1739* (2013.01); *A61B 17/848* (2013.01); *A61B 17/863* (2013.01); *A61B 17/8897* (2013.01); *A61B 17/1775* (2016.11); *A61B 17/8615* (2013.01); *A61B 17/8635* (2013.01); *A61B 2090/062* (2016.02)

(58) Field of Classification Search
CPC combination set(s) only.
See application file for complete search history.

(56) References Cited

U.S. PATENT DOCUMENTS

| 5,139,500 A | 8/1992 | Schwartz |
|---|---|---|
| 8,128,662 B2 | 3/2012 | Altarac et al. |

(Continued)

OTHER PUBLICATIONS

International Search Report for PCT/US2014/050498 dated Feb. 3, 2015.
Written Opinion for PCT/US2014/050498 dated Feb. 3, 2015.

*Primary Examiner* — Sameh Boles
(74) *Attorney, Agent, or Firm* — Heslin Rothenberg Farley & Mesiti P.C.

(57) ABSTRACT

A method for fusing bones using a guide pin and a fastener is disclosed. The method includes inserting a guide pin into two bones. The guide pin including at least one radial marking. The method also including imaging the two bones and guide pin and analyzing the position of the at least one radial marking of the guide pin relative to the two bones. In addition, the method includes selecting a fastener, inserting a drill over the guide pin, drilling an opening through at least one of the two bones, and inserting the fastener into the opening. The guide pin may include an exterior surface with a first end and a second end, a cutting edge at the first end, and at least one radial marking near the first end. A system including a guide pin, a fastener, and a drill is also disclosed.

15 Claims, 12 Drawing Sheets

(51) Int. Cl.
*A61B 17/17* (2006.01)
*A61B 90/00* (2016.01)

(56) References Cited

U.S. PATENT DOCUMENTS

2013/0090658 A1  4/2013  Kam
2014/0066932 A1* 3/2014  Appenzeller ...... A61B 17/1725
                                                606/64

* cited by examiner

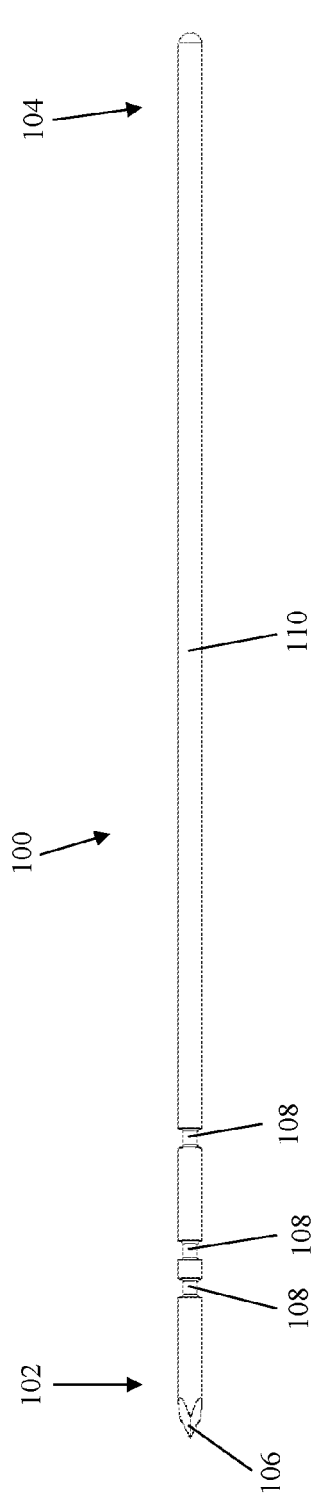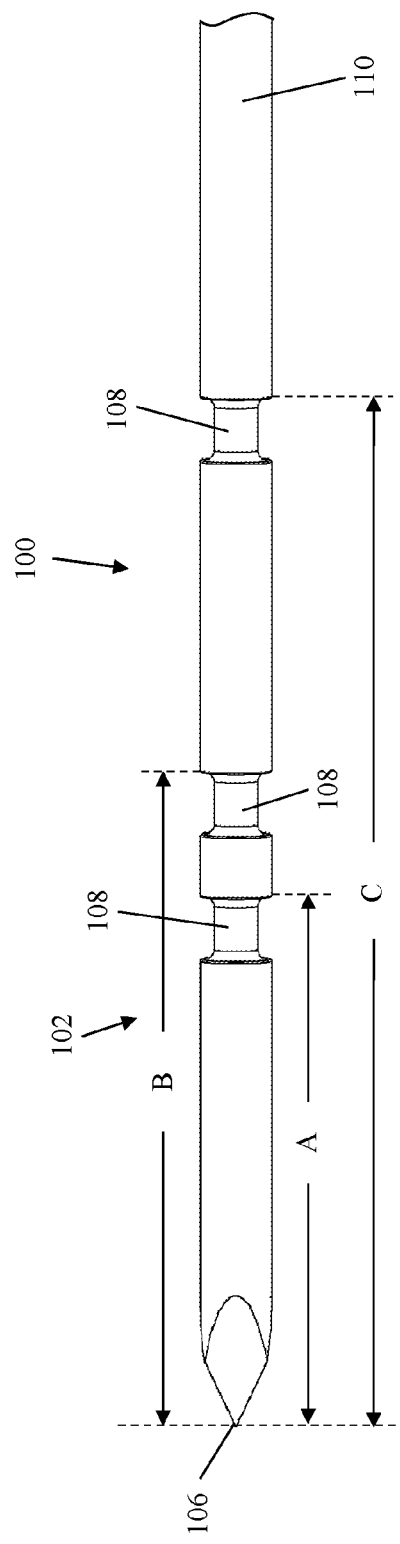
FIG. 2
FIG. 3

DEVICES AND METHOD OF ACHIEVING BONE FUSION

CROSS-REFERENCE TO RELATED APPLICATION

This application is a divisional application of U.S. patent application Ser. No. 13/964,535, filed Aug. 12, 2013, and entitled "DEVICES AND METHOD OF ACHIEVING BONE FUSION," which is hereby incorporated herein by reference in its entirety.

FIELD OF THE INVENTION

The present invention relates generally to general surgery, orthopaedic implants used for achieving bone fusion. More specifically, but not exclusively, the present invention relates to a method for achieving bone fusion using guide pins and fasteners.

BACKGROUND OF THE INVENTION

Bone fusion techniques generally leave the physician unable to view the positioning or location of the fusion implants during the surgical procedure and may result in decreased probability of fusion at the desired location or in the desire position. Generally, in small bone surgery screws are used across a joint or fracture site and the surgeon will need to use inaccurate depth gages, depth probes or other tools in an attempt to determine what size screw is needed after an opening in the bones has been drilled. Current methods generally include trial and error for placement of the screw and determining proper screw length.

SUMMARY OF THE INVENTION

Aspects of the present invention provide a guide pin and bone fastener for use in a method of fusing bones.

In one aspect, provided herein is a guide pin that includes an exterior surface with a first end and a second end, a cutting edge on at least the first end, and at least one radial marking near the first end.

In another aspect, provided herein is a system for bone fusion including a guide pin, fastener, and drill. The guide pin has an exterior surface with at least one cutting end. The guide pin also includes at least one radial marking near the at least one cutting end. The fastener includes a head portion with a superior end and an inferior end and a shaft portion that has a smooth end and a threaded end. The smooth end of the shaft portion is joined to the inferior end of the head portion. The drill is configured to slidingly engage the exterior surface of the guide pin to drill an opening.

In yet another aspect, provided herein is a surgical method for fusing bones that includes the steps of inserting a guide pin into two bones. The guide pin has at least one radial marking. The method also includes the step of imaging the two bones and the guide pin and the step of analyzing the position of the at least one radial marking of the guide pin relative to the two bones. In addition, the method includes the step of selecting a fastener, inserting a drill over the guide pin, drilling an opening through at least one of the two bones, and inserting the fastener into the opening.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 2 is a side view of the guide pin of FIG. 1, in accordance with an aspect of the present invention;

FIG. 3 is a side view of the first end of the guide pin of FIG. 1, in accordance with an aspect of the present invention;

DETAILED DESCRIPTION FOR CARRYING OUT THE INVENTION

Generally stated, disclosed herein is one embodiment of a guide pin and a fastener. Further, a surgical method for using the guide pin and fastener is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current devices and methods are described herein with reference to use with the bones of the foot, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices and methods, and the aspects, components, features and the like thereof, described herein with respect to the right foot may be mirrored so that they likewise function with the left foot. Further, the devices and methods, and the aspects, components, features and the like thereof, disclosed herein are described with respect to the foot for brevity purposes, but it should be understood that the devices and methods may be used with other bones of the body having similar structures, for example the upper extremity, and more specifically, with the bones of the wrist, hand, and arm.

Figure 1:
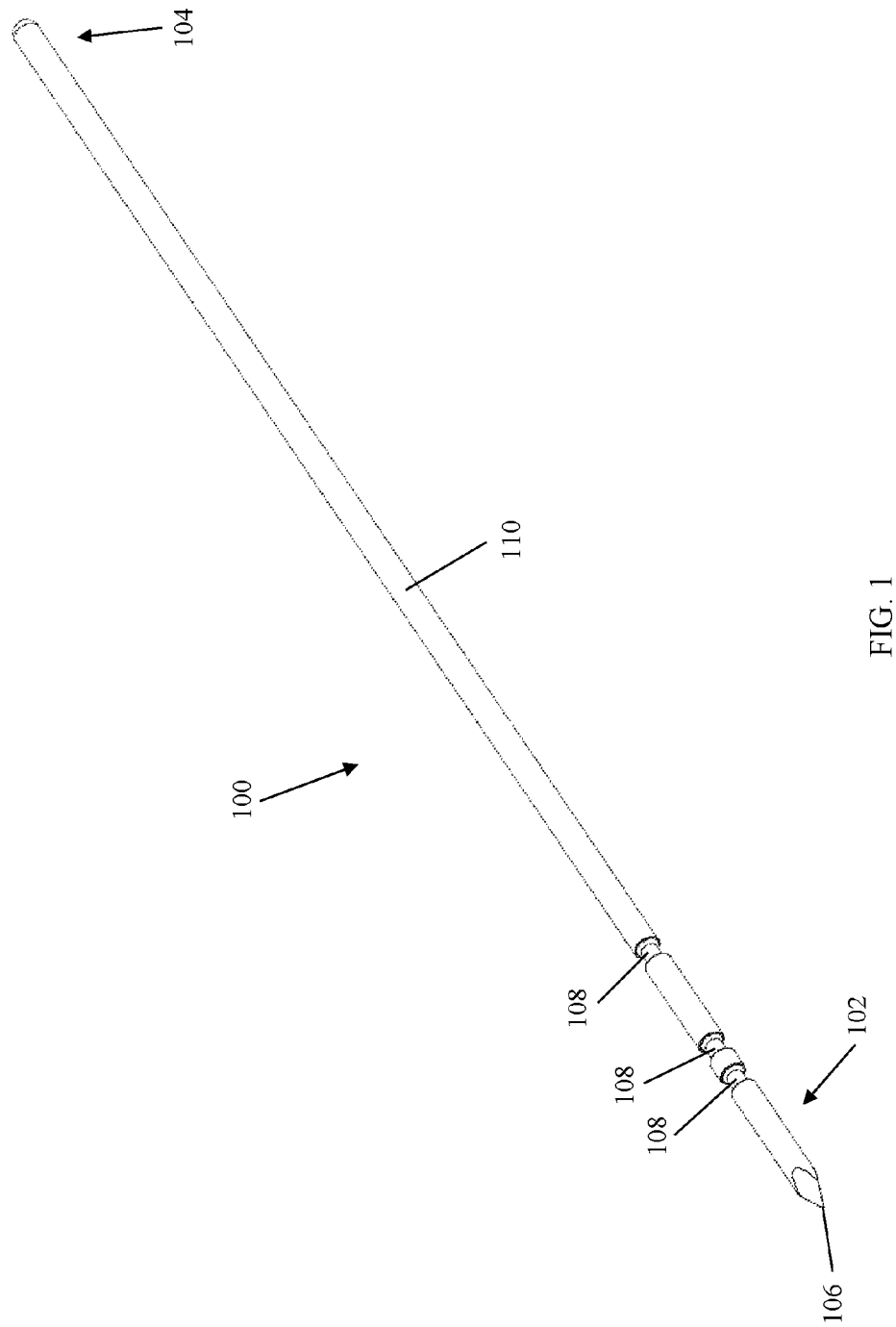
FIG. 1 is a perspective view of one embodiment of a guide pin, in accordance with an aspect of the present invention.

Referring to the drawings, wherein like reference numerals are used to indicate like or analogous components throughout the several views, and with particular reference to FIGS. 1-3, there is illustrated an exemplary embodiment guide pin 100. The guide pin 100 may be, for example, a cylindrical rod including a first end 102 and a second end 104. The terms "guide pin," "cylindrical rod," "guide wire," and "pin" may be used interchangeably herein as they essentially describe the same device. The first end 102 may include a tip 106 and the tip 106 may be a sharp cutting point. The tip 106 may penetrate a patient's soft tissue and/or bone. In alternative embodiments, the guide pin 100 may have a tip 106 at the first end 102 and the second end 104. The guide pin 100 as shown in FIGS. 1-3 may also include a smooth exterior surface 110. In alternative embodiments, the exterior surface 110 may include threads (not shown) adjacent to the tip 106.

The guide pin 100 may also include at least one circumferential indentation, notch, radial marking or recess 108 near the first end 102. The terms "indentation," "notch," "radial marking" and "recess" may be used interchangeably herein as they essentially describe the same structure. In the depicted embodiments, the guide pin 100 includes three recesses 108, although any number of recesses is contemplated, for example, two or four recesses 108. In one embodiment the recesses 108 may be positioned at a distance (A), for example, about 5 mm to 20 mm, at a distance (B), for example, about 10 mm to 30 mm, and at a distance (C), for example, about 20 mm to 40 mm from the tip 106 of the guide pin 100, as shown in FIG. 3. In the depicted embodiment, shown in FIGS. 1-3, the distances of the recesses 108 from the tip 106 may be 16 mm for (A), 20 mm for (B) and 32 mm for (C). The distances (A), (B), and (C) may be measured from the tip 106 to the distal end of the recesses 108, or the side of the recesses 108 closest to the second end 104. The distances (A), (B), and (C) may correspond, for example, to the various thread lengths of a given sized bone screw, described in greater detail below, that may be used for insertion across the joint. The guide pin 100 may also be used to measure the overall length of the screw that is needed for insertion into the bones or across a joint or bone fracture, as described in greater detail below. Thus, the overall length of the screw and the thread length of the screw may be selected using the guide pin 100 to ensure the two bone fragments are adequately compressed and joined together. In addition, the recesses 108 may have a width of, for example, 1 mm to 3 mm and may be recessed a depth of, for example, about 0.20 mm to 0.50 mm from the exterior surface 110. The recesses 108 may also be circumferential around the guide pin 100 or only extend around a portion or partially around the guide pin 100. The guide pin 100 may also be used as a drill guide for inserting a drill into a patient's bone or across a patient's joint.

By way of specific example, the guide pin 100 may be of the type described above with reference to FIGS. 1-3, but may only include, for example, two recesses 108 positioned at distances (B) and (C). The distances (B) and (C) may correspond, for example, to two different size thread lengths of a given sized bone screw, as described in greater detail below. In this embodiment if neither of the recesses 108 at distances (B) or (C) crosses the joint space, then a bone screw with a shorter thread length than the thread lengths corresponding to distances (B) and (C) will be selected.

Figure 4:
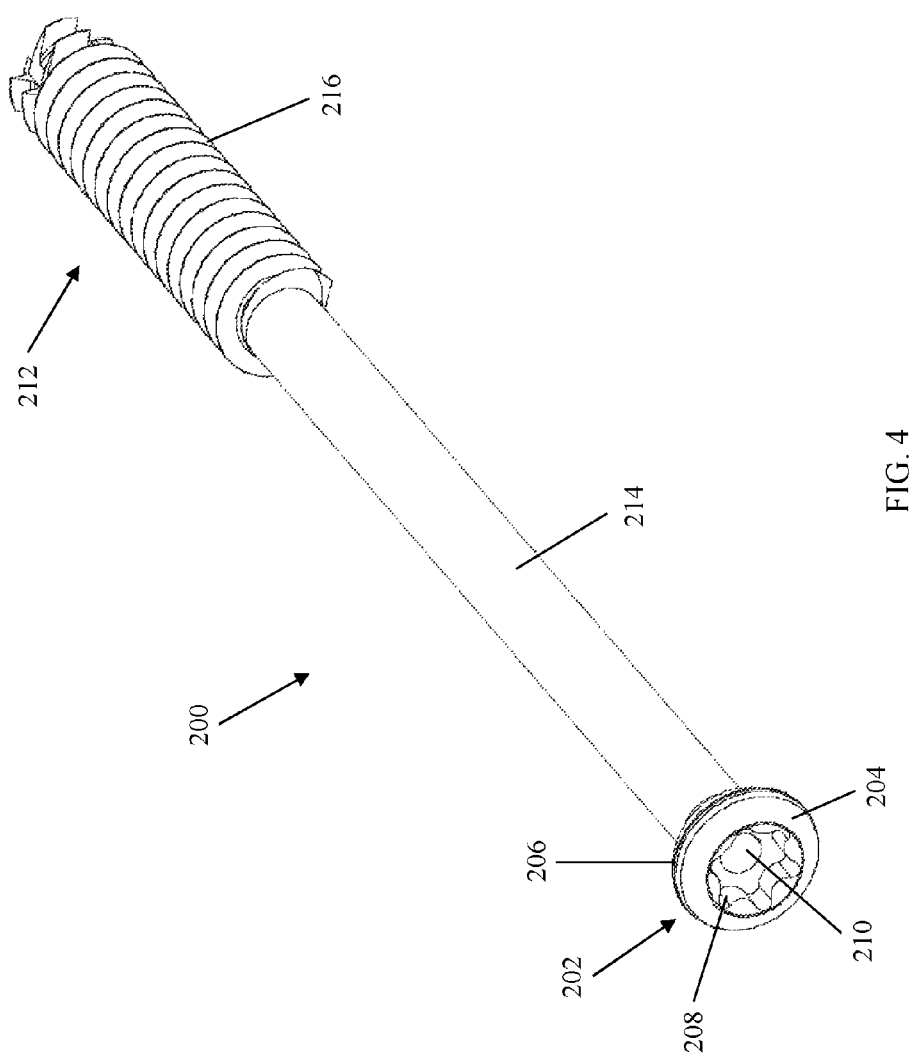
FIG. 4 is a top perspective view of one embodiment of a fastener, in accordance with an aspect of the present invention.
Figure 5:
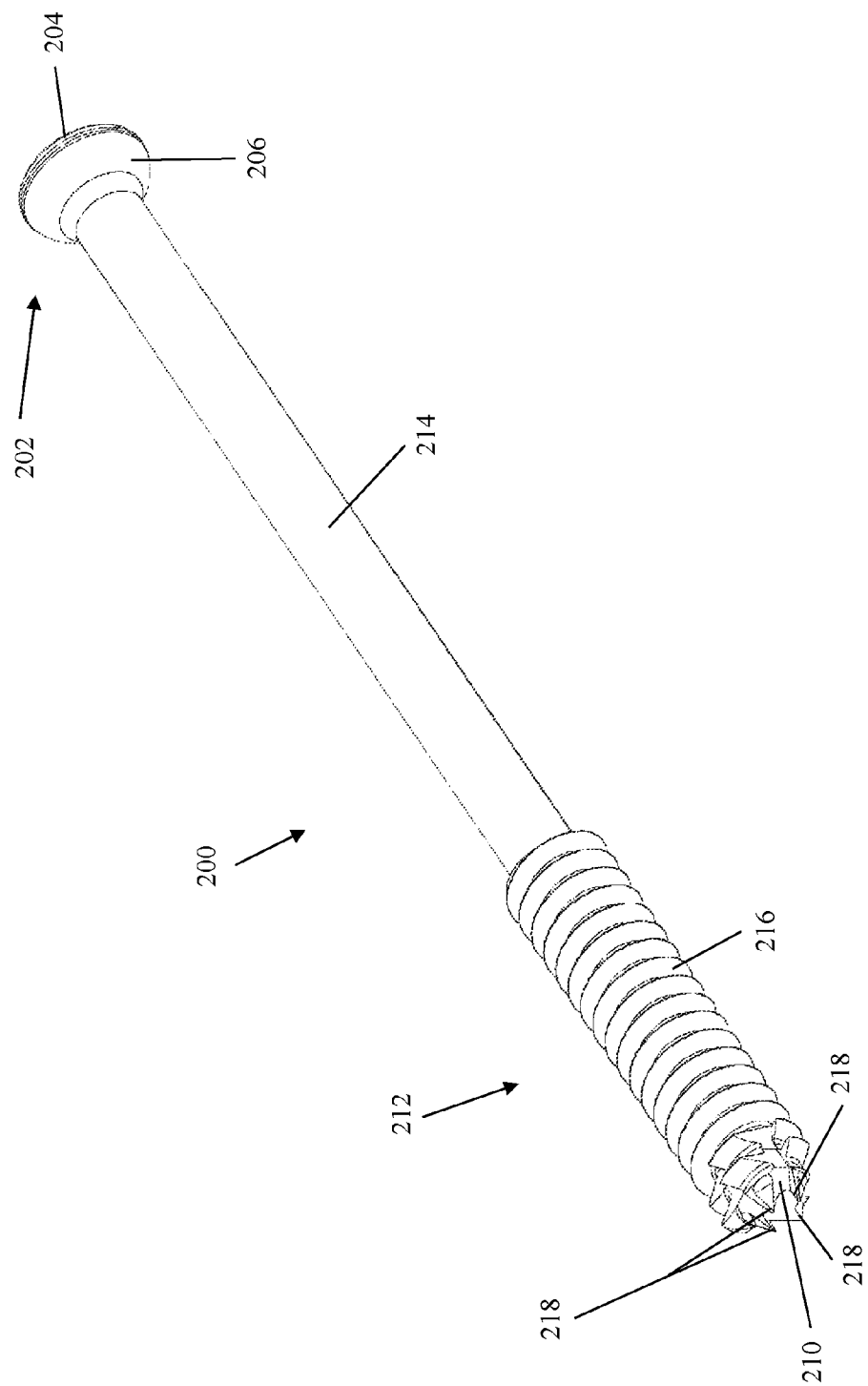
FIG. 5 is a bottom perspective view of the fastener of FIG. 3, in accordance with an aspect of the present invention.
Figure 6:
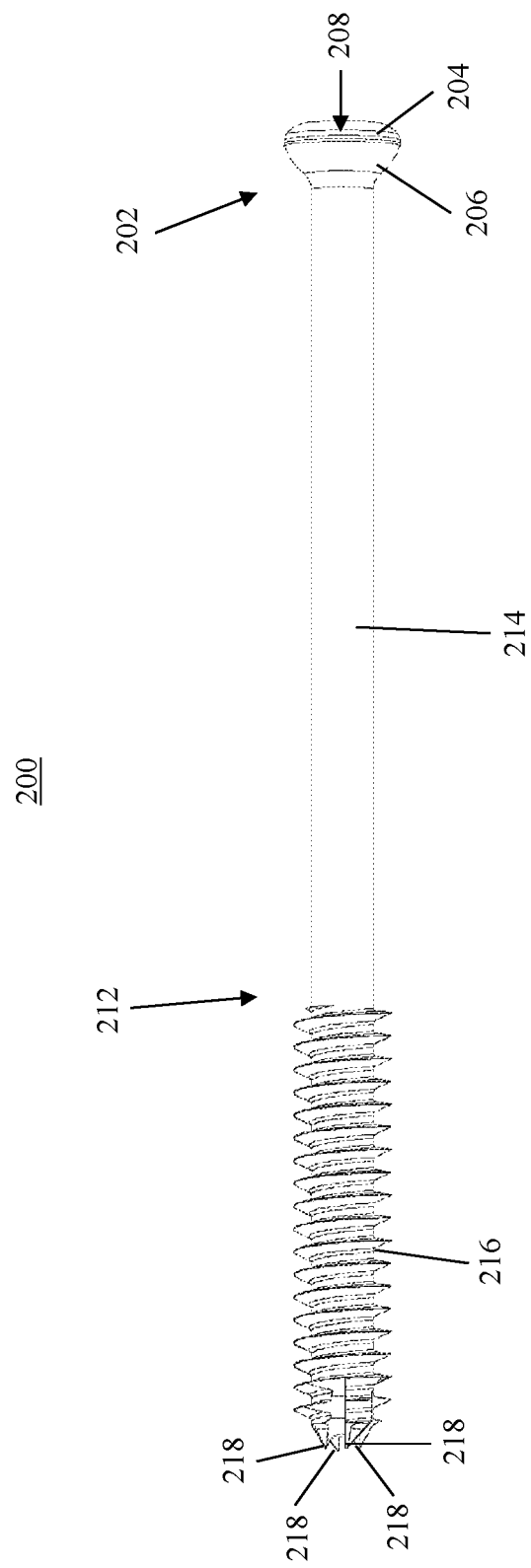
FIG. 6 is a side view of the fastener of FIG. 3, in accordance with an aspect of the present invention.
Figure 7:
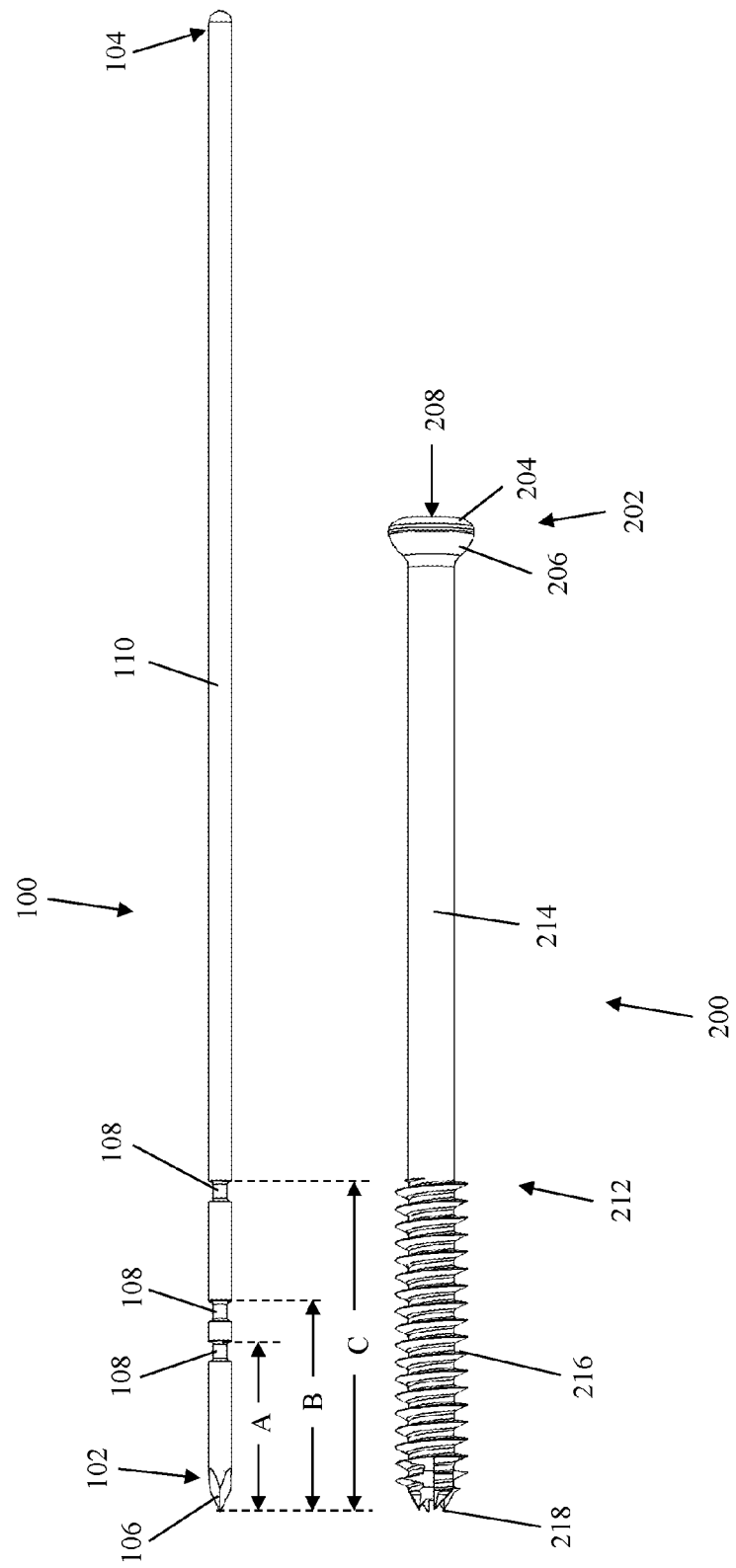
FIG. 7 is a side view of the guide pin of FIG. 1 aligned with the fastener of FIG. 3, in accordance with an aspect of the present invention.
Figure 10:
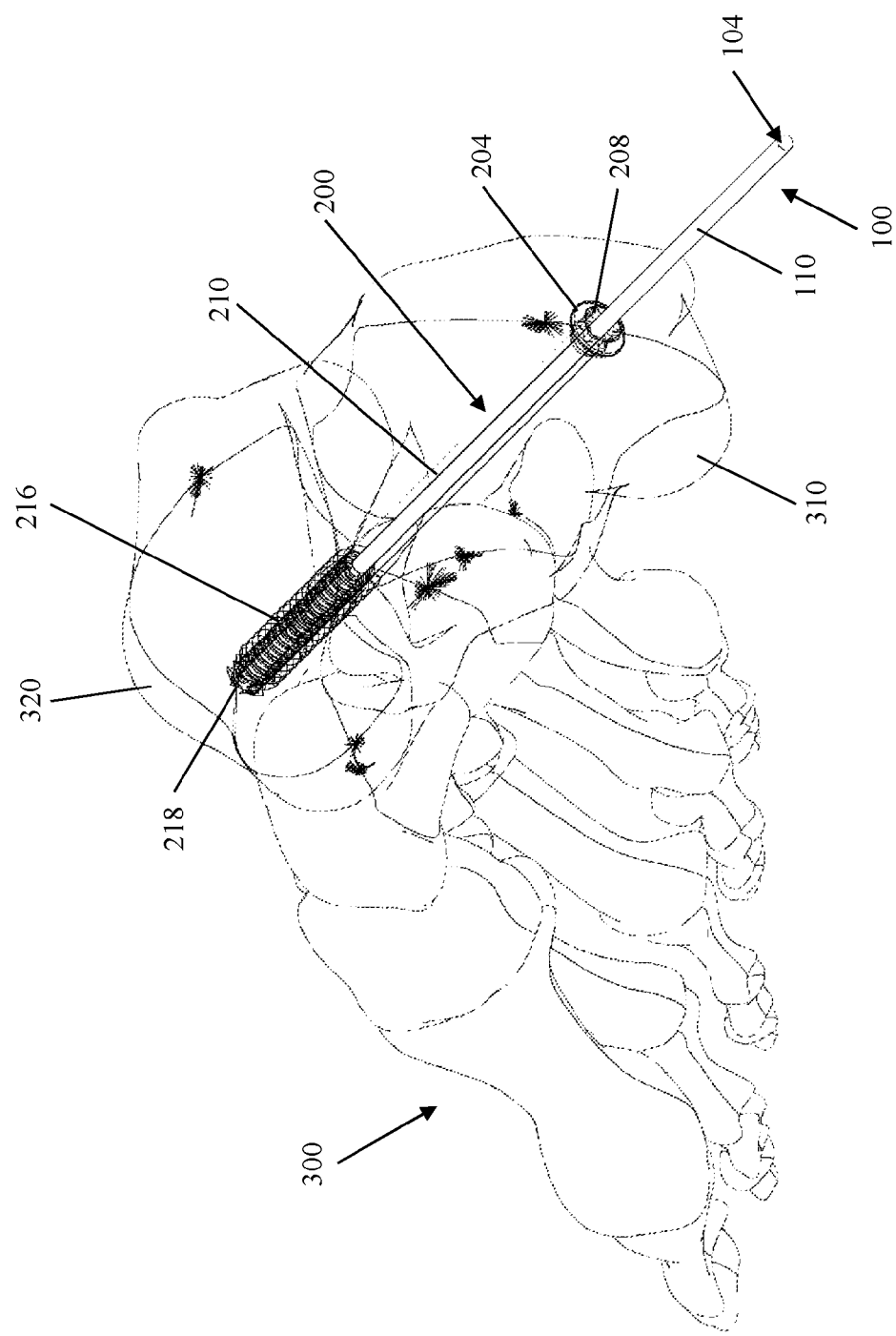
FIG. 10 is a posterior view of the right foot of FIG. 9 with the fastener of FIG. 4 inserted over the guide pin of FIG. 1, in accordance with an aspect of the present invention.
Figure 11:
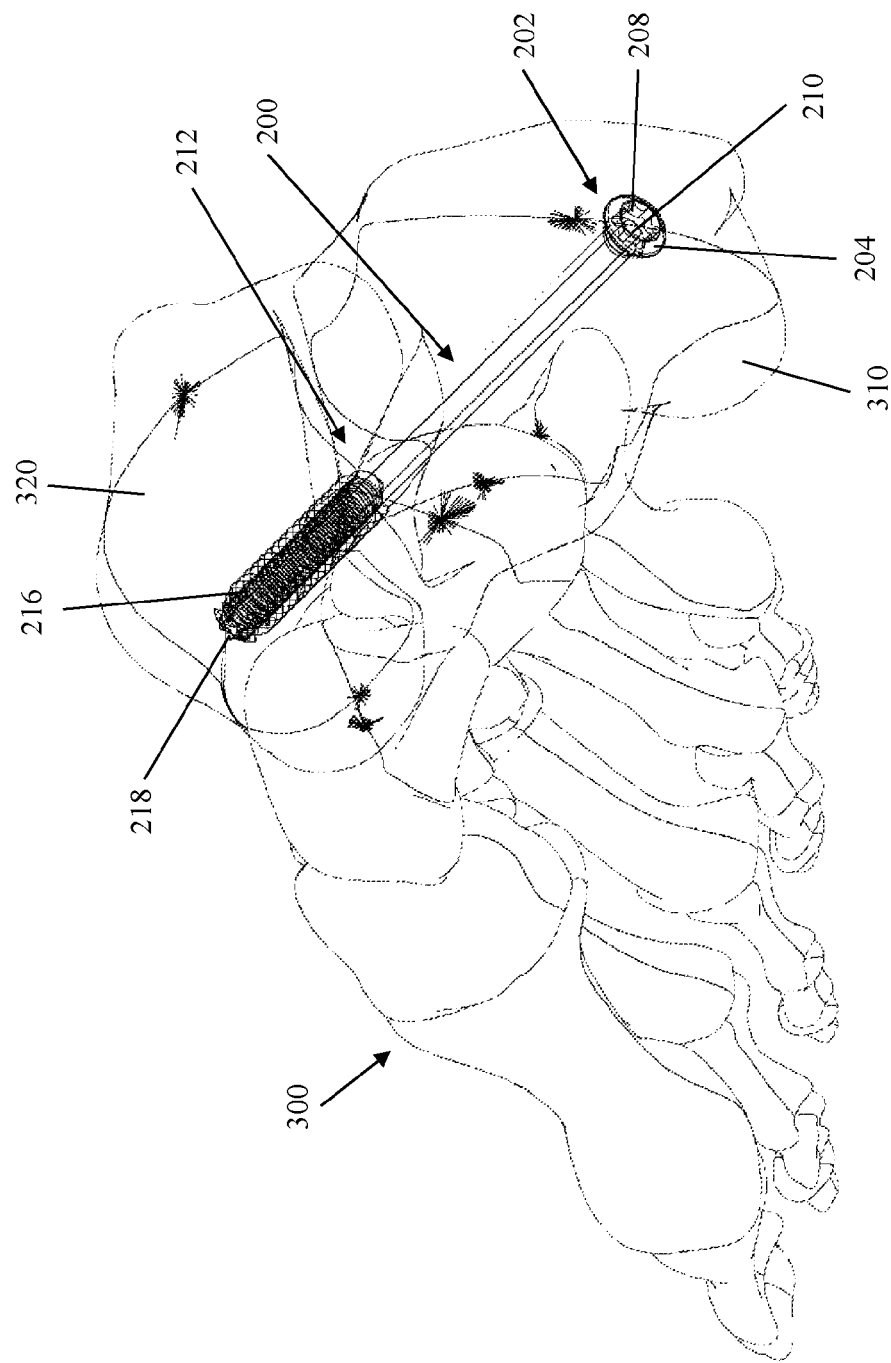
FIG. 11 is a posterior view of the right foot of FIG. 9 after removal of the guide pin, in accordance with an aspect of the present invention.
Figure 12:
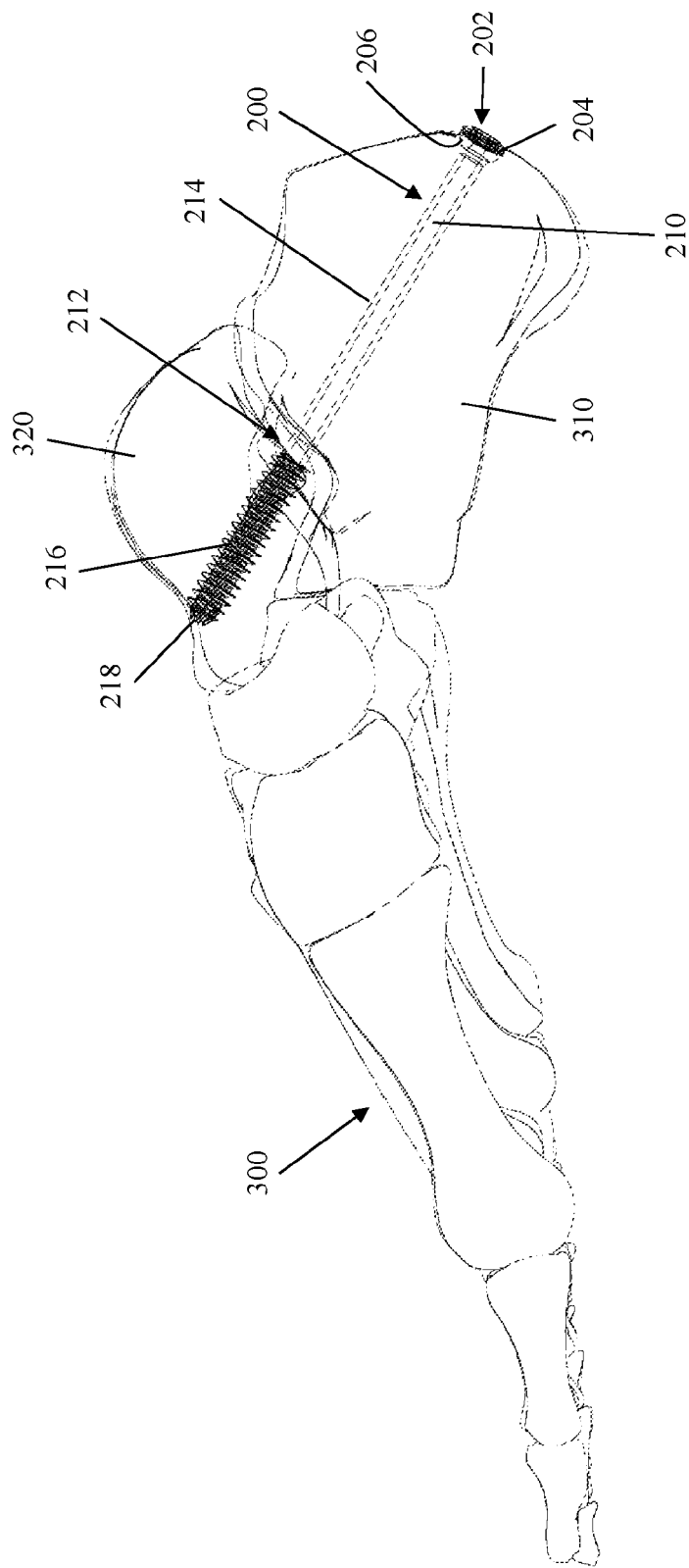
FIG. 12 is a medial view of the right foot of FIG. 11, in accordance with an aspect of the present invention.

Referring now to FIGS. 4-6, a fastener 200 is shown. The terms "bone screw," "fastener," "fixator," "elongate member," and "screw" may be used interchangeably herein as they essentially describe the same type of device. The bone screw 200 may include a head portion 202 and a shaft portion 212. The head portion 202 may include a superior end 204 and an inferior end 206. The superior end 204 of the head portion 202 may have a tool engagement opening 208 and a cannulation or center hole 210, as shown in FIG. 4. The tool engagement opening 208 may have a multi-lobed shape as shown in FIG. 4, although other polygonal shapes are also contemplated. The shaft portion 212 may include a smooth end 214 and a threaded end 216 for engaging a patient's bone, as seen in FIGS. 10-12. The bone screw 200 may be, for example, available in multiple sizes with threaded ends 216 of various lengths to correspond to the distances (A), (B), and (C) of the guide pin 100. By way of specific example, as shown in FIG. 7, the threaded end 216 of fastener 200 corresponds to the distance (C) of the guide pin 100. The threaded end 216 of the shaft portion 212 may also include at least one cutting tip 218, as shown in FIG. 5, to assist in insertion into the patient's bone. In the embodiment shown in FIG. 5, the threaded end 216 includes four cutting tips 218.

Figure 8:
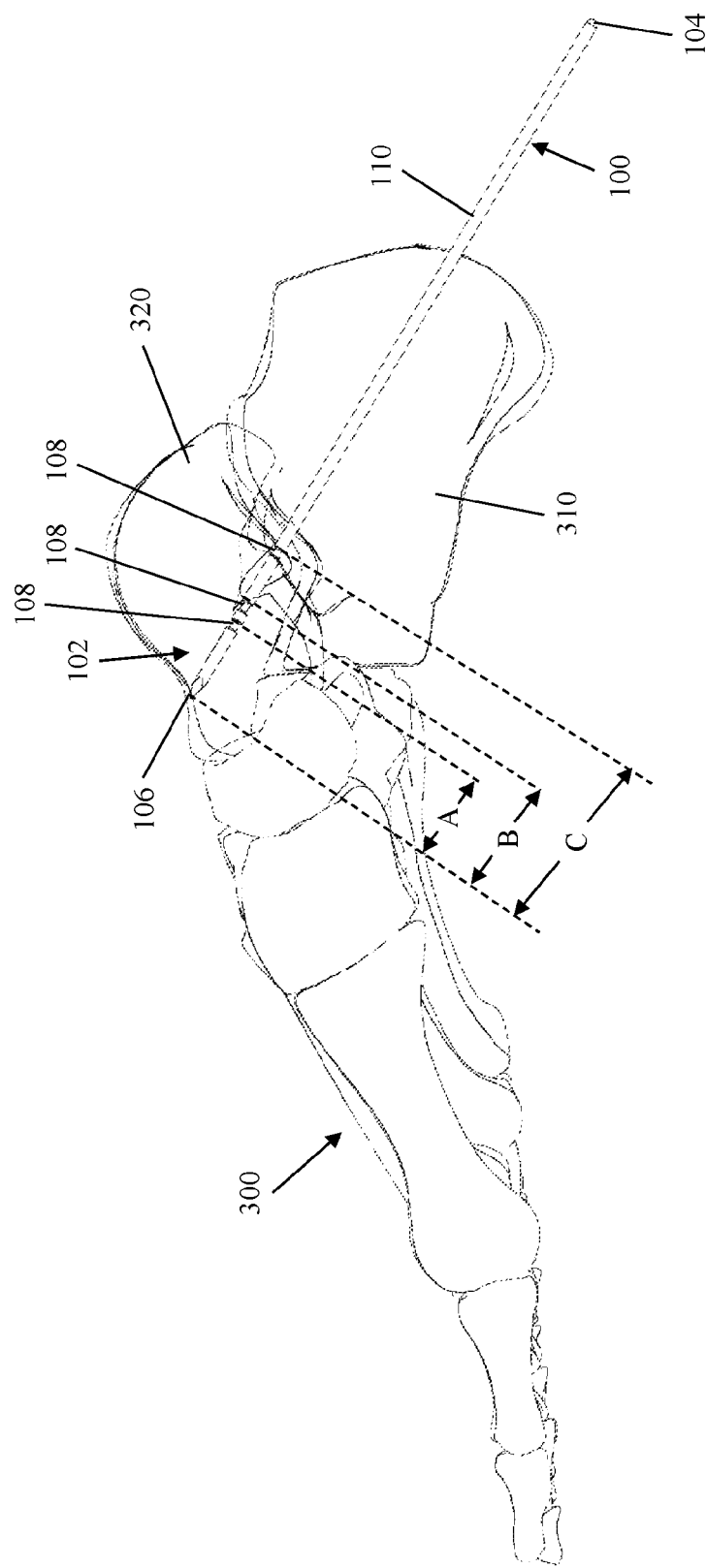
FIG. 8 is a medial view of the bones of a right foot with the guide pin of FIG. 1 inserted through two bones, in accordance with an aspect of the present invention.

A surgical method using the guide pin 100 and fastener 200 is shown in FIGS. 8-13. As shown in FIG. 8, after exposure of the surgical site, a guide pin 100 is inserted into two adjacent bones in the foot 300, for example, through the calcaneous bone 310 and into the talus bone 320 crossing the joint space between the bones. After insertion of the guide pin 100, at least one image, for example, using fluoroscopy, may be taken of the bones 310, 320 and the guide pin 100. The at least one image may be used to check the position of the guide pin 100, the position of the radial markings 108, and to ensure that the guide pin 100 crosses the space between the bones 310, 320. The image will be used to determine the location of the recesses 108 relative to the joint space, for example, the joint space between the bones 310, 320. The location of the recesses 108 will then be analyzed to determine the necessary thread length 216 of the bone screw 200 for insertion, alignment, and adequate compression across the joint. The positioning of the recesses 108 of the guide pin 100 allows the surgeon to determine the thread length of the screw. For example, as shown in FIG. 8, the recesses 108 at distance A, B and C all extend through the joint space and into the bone 320. Based on the positioning of the recess 108 at distance C, a screw having a thread length 216 of distance C, as shown in FIG. 7, should be selected to ensure the threads of the screw all extend past the bone joint space. Next, a depth gauge may be aligned with the portion of the guide pin 100 extending out of the patient's incision or the screw entry point after the desired position of the guide pin 100 is obtained. The depth gauge may be used to measure the overall length of the screw that is needed. A screw may then be selected based on the measurements for the thread length 216 and overall screw length for insertion into a bone or across a joint as well as to ensure proper fusion orientation of the bones.

Figure 9:
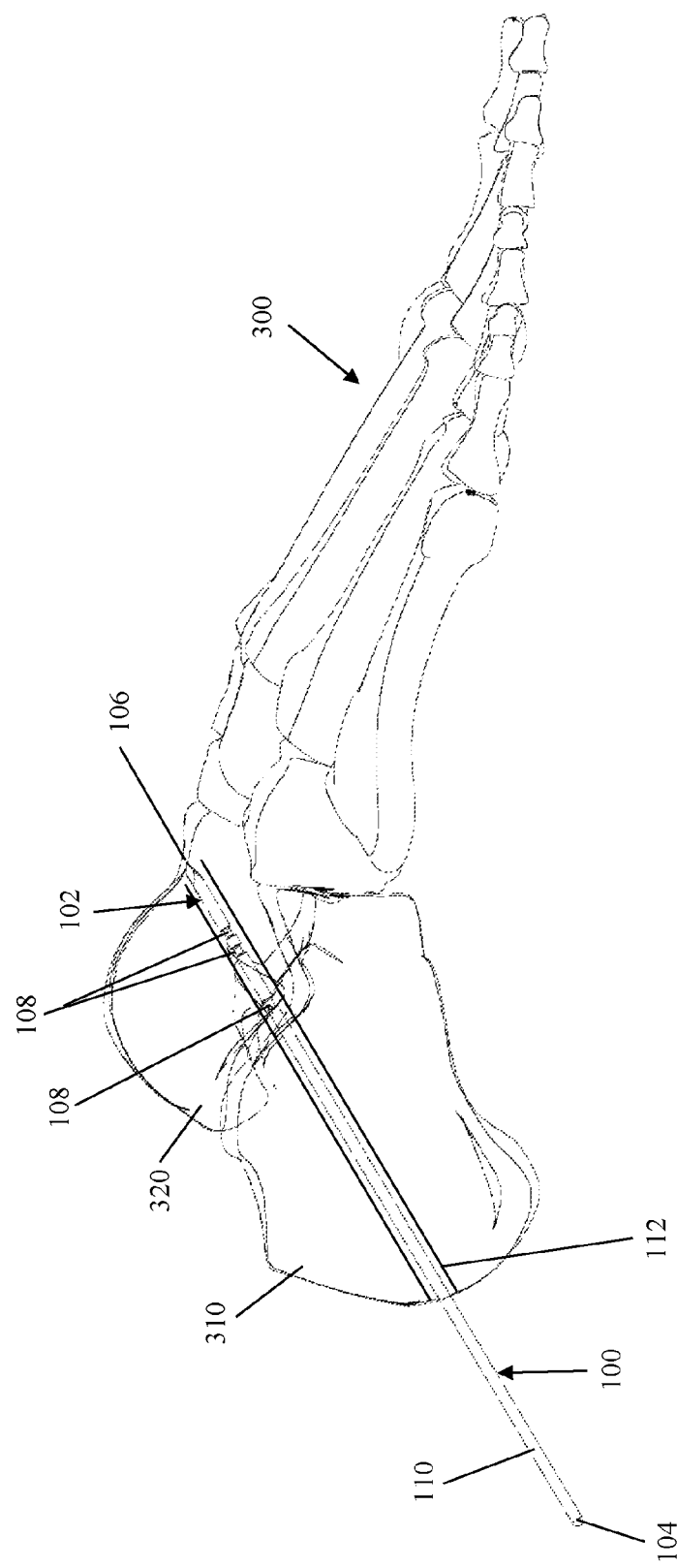
FIG. 9 is a lateral view of the right foot of FIG. 8, in accordance with an aspect of the present invention.

Once the bone screw 200 is selected, a drill may be inserted over the guide pin 100 and guided along the exterior surface 110 of the guide pin 100 from the second end 104 to the first end 102 to create an opening 112 for insertion of a bone screw 200, as shown in FIG. 9. A drill guide and/or tissue protector, not shown, may also be used during the insertion of the guide pin 100 and/or during the drilling of the opening 112 to assist in guiding the insertion of the guide pin 100 and the screw 200 as well as to protect the surrounding soft tissue. After the opening 112 is drilled, the drill may be removed and the drill guide as well as the tissue protector may be removed. Then the selected bone screw 200 may be inserted into the opening 112 by aligning the cannulation 210 of the bone screw 200 with the guide pin 100 and threading the screw 200 into the bones over the guide pin 100, as shown in FIG. 10. As the screw 200 is inserted into the patient's bones 310, 320 a compression force across the joint or fracture should be maintained. Once the bone screw 200 is fully inserted into the patient's bones 310, 320, the guide pin 100 may be removed. As shown in FIG. 12, the bone screw 200 will pass through the joint between the bones 310, 320 to hold the bones 310, 320 in a desired position for bone fusion.

Figure 13:
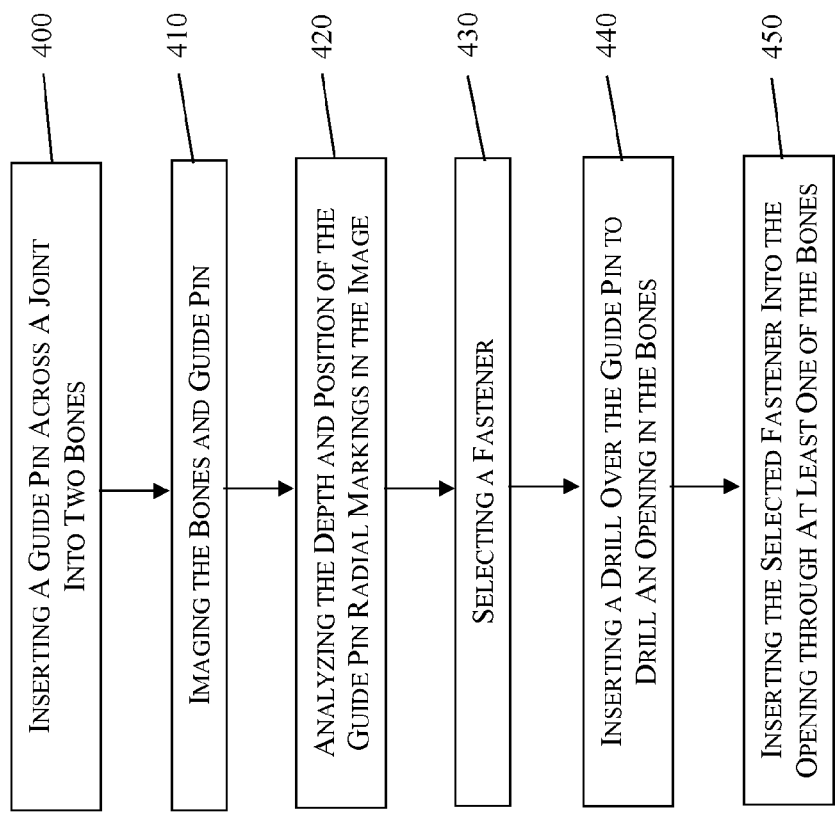
FIG. 13 depicts one embodiment of a surgical method for using the guide pin of FIG. 1 to insert a fastener, in accordance with an aspect of the present invention.

Referring now to FIG. 13, the surgical method may include inserting a guide pin across the space between two bones 400. Next an image of the bone joint space and guide pin may be taken 410. The method may also include analyzing the depth and position of the radial markings of the guide pin 420 to determine the necessary thread length of the fastener to ensure proper bone positioning post implantation. Then a fastener may be selected 430 using the measured thread length and a drill may be selected and inserted over the guide pin to drill an opening in the bones 440. After the opening is drilled the selected fastener may be inserted into the bones and across the joint through the opening 450.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A surgical method, comprising:
   obtaining a bone fusion system comprising:
      a guide pin; and
      a fastener;
   inserting the guide pin into two bones, the guide pin having at least one radiolucent radial marking;
   imaging the two bones and the guide pin;
   analyzing the position of the at least one radiolucent radial marking of the guide pin relative to the two bones;
   selecting the fastener;
   inserting a drill over the guide pin;
   drilling at least one opening through at least one of the two bones; and
   inserting the fastener into the at least one opening.

2. The surgical method of claim 1, wherein the guide pin further comprises:
   an exterior surface with at least one cutting end; and
   wherein the at least one radiolucent radial marking is proximal to the at least one cutting end; and
   wherein the fastener comprises:
      a head portion with a superior end and an inferior end; and
      a shaft portion with a smooth end and a threaded end, the smooth end of the shaft portion configured to join to the inferior end of the head portion.

3. The surgical method of claim 1, wherein the drill is configured to slidingly engage the exterior surface of the guide pin to drill the opening.

4. The surgical method of claim 1, wherein selecting the fastener comprises:
   determining a thread length of the fastener based on the position of the at least one radiolucent radial marking relative to a space between two bones.

5. The surgical method of claim 4, wherein selecting the fastener further comprises:
   determining an overall fastener length using a depth gauge to measure the portion of the guide pin extending out of a screw entry point.

6. The surgical method of claim 5, wherein selecting the fastener comprises using the determined thread length and overall fastener length.

7. The surgical method of claim 1, further comprising:
   inserting the fastener over the guide pin.

8. The surgical method of claim 4, wherein the at least one radiolucent radial marking includes a first radial marking configured to correspond to a first thread length of the fastener, and a second radial marking configured to correspond to a second thread length of the fastener.

9. The surgical method of claim 8, wherein selecting the fastener comprises:
    selecting the fastener with a thread length corresponding to the at least one radiolucent radial marking that is positioned within a second bone of the two bones and positioned closest to the space between the two bones.

10. A method of use, comprising:
    obtaining a bone fusion system comprising:
        a guide pin, the guide pin having:
            an exterior surface with a first end and a second end;
            a cutting edge on at least the first end; and
            at least two radiolucent radial markings positioned between the first end and a midpoint of the exterior surface, wherein the at least two radiolucent radial markings comprises:
                a first radiolucent radial marking positioned a first distance from the cutting edge; and
                a second radiolucent radial marking positioned a second distance from the cutting edge;
        wherein the first radiolucent radial marking is positioned nearest the cutting edge, and the second radiolucent radial marking is positioned furthest from the cutting edge; and
        wherein the at least two radiolucent radial markings comprise:
            a center section with a first end and a second end extending a distance therebetween, wherein the distance defines a width;
            a first beveled portion extending from the exterior surface of the guide pin to the first end of the center section; and
            a second beveled portion extending from the exterior surface of the guide pin to the second end of the center section; and
        a bone screw;
    inserting the guide pin into at least two bones;
    imaging the at least two bones and the inserted guide pin;
    measuring the position of the guide pin;
    selecting a bone screw;
    preparing a hole that extends straight through the at least two bones; and
    inserting the bone screw into the hole.

11. The method of use of claim 10, wherein the cutting edge of the guide pin further comprises a pointed tip, wherein the pointed tip is configured to be inserted into the at least two bones.

12. The method of use of claim 10, wherein preparing the hole comprises:
    selecting a drill bit; and
    placing the drill bit over the guide pin.

13. The method of use of claim 12, wherein preparing the hole further comprises drilling a hole through the at least two bones.

14. The method of use of claim 10, wherein selecting the bone screw comprises:
    determining a thread length of the bone screw, wherein the thread length is determined by the position of the first radiolucent radial marking or the second radiolucent radial marking.

15. The method of use of claim 14, wherein determining a thread length further comprises:
    measuring a distance from the pointed tip to the first radiolucent radial marking or the second radiolucent radial marking that is located within a second bone of the at least two bones, and is positioned closest to a space between the at least two bones.

* * * * *